United States Patent [19]
Hippenmeyer et al.

[11] Patent Number: 5,972,666
[45] Date of Patent: Oct. 26, 1999

[54] ASSEMBLY-DEFICIENT HERPESVIRUS VACCINE

[75] Inventors: Paul J Hippenmeyer, St. Louis; Anne M Rankin, Ballwin; Verne A Luckow, Chesterfield, all of Mo.

[73] Assignee: G. D. Searle & Co., Chicago, Ill.

[21] Appl. No.: 08/687,820

[22] Filed: Jul. 26, 1996

[51] Int. Cl.$^6$ .............. C12N 15/00; C12N 7/04; A01N 63/00; A61K 39/245

[52] U.S. Cl. .............. 435/172.3; 424/93.2; 424/230.1; 424/231.1; 424/229.1; 435/236; 435/325

[58] Field of Search .............. 424/93.2, 230.1, 424/231.1, 229.1; 435/172.3, 236, 325

[56] References Cited

U.S. PATENT DOCUMENTS 5,384,122  1/1995  Cunningham et al. ............. 424/231.1

OTHER PUBLICATIONS

Rixon F. et al. Insertion of DNA at a unique restriction enzyme site engineered for vector purposes into the genome of herpes simplex virus type I, J. Gen. Virol. 71:2931–2939, 1990.

*Primary Examiner*—Jeffrey Stucker
*Assistant Examiner*—Hankyel T. Park
*Attorney, Agent, or Firm*—Dennis A. Bennett; Joseph W. Bulock

[57] ABSTRACT

A vaccine is described which comprises an assembly-deficient herpesvirus. The mutant herpesvirus is capable of infecting and undergoing DNA replication in the cells of a susceptible mammal, but is defective in capsid assembly and formation of mature virion particles. The assembly-deficient herpesvirus is avirulent and capable of generating a protective immune response in a vaccinated mammal.

14 Claims, 6 Drawing Sheets

A. pMON15839A

B. pMON15840

C. pMON27005

D. pMON15835

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 62 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic DNA"

(xi) SEQUENCE DESCRIPTION: SEQ ID NO:1:

```
TCCGGAATTT AAATCAATTG GGCGCGCCTT AATTAACAAG CATGCTGGGT TTAAACTGAT      60

CA                                                                    62
```

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic"

(xi) SEQUENCE DESCRIPTION: SEQ ID NO:2:

```
GGGCGAGTTG GCATTGGATC                                                 20
```

(2) INFORMATION FOR SEQ ID NO:3:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "SYNTHETIC"

-continued (xi) SEQUENCE DESCRIPTION: SEQ ID NO:3:

AGACCGAGGG CAGGTAGTT                                                19

(2) INFORMATION FOR SEQ ID NO:4:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE:
        (A) DESCRIPTION: /desc = "SYNTHETIC"

(xi) SEQUENCE DESCRIPTION: SEQ ID NO:4:

Arg Lys Gly Ser Gly Arg Val Gly Pro Asp Gly Ala Ala Pro
1               5                   10

ASSEMBLY-DEFICIENT HERPESVIRUS VACCINE

FIELD OF THE INVENTION

This invention is in the field of viral vaccines, and specifically relates to the generation of assembly-deficient mutant herpesviruses, vaccines comprising assembly-deficient mutant herpesviruses, and methods for the production and manufacture of assembly-deficient herpesvirus vaccines.

BACKGROUND OF THE INVENTION

There is a great need for therapies for the treatment of viral diseases. While antiviral drugs such as zidovudine, used in the treatment of human immunodeficiency virus (HIV), and drugs such as ganciclovir, acyclovir, and foscarnet are used in the treatment of herpesvirus infections, significant side effects often limit their effectiveness. The selection and spread of drug-resistant viruses also limits the effectiveness of small molecular weight antiviral drugs. This is a particularly significant problem for drugs targeted against RNA viruses such as HIV, which have a relatively high mutation rate compared to most DNA viruses.

Antiviral vaccines are a viable alternative to postinfection antiviral drug treatments. Ideally, antiviral vaccines protect against primary disease and recurring infections. Efficacy against a particular disease is crucial to the development of a vaccine strategy. Regulatory concerns, particularly related to the safety of vaccines intended for prophylactic use in healthy individuals, must also be considered.

While herpesvirus vaccines have been an active area of both academic and commercial interest, induction of a good, protective immune response in humans has been challenging [R. L. Burke, *Current Status of HSV Vaccine Development*, in The Human Herpesviruses, 367–379, (B. Roizman, R. J. Whitley and C. Lopez, eds. 1993)]. Live virus vaccines have the risk of establishing latency and reactivating. Live virus vaccines also have the potential of recombining with natural isolates.

Attenuated recombinant viruses and subunit vaccines have been investigated to avoid these risks. Meignier et al describe a recombinant virus resulting from the removal of a region of herpes simplex virus type 1 (HSV-1) required for virulence and the insertion of herpes simplex virus type 2 (HSV-2) glycoprotein genes [J. Infect. Dis., 158:602–614 (1988)]. The viruses had reduced pathogenicity and induced immunity in a number of animal models.

More recently, recombinant herpes simplex viruses with deletions in essential immediate early or early genes have been described. These recombinant viruses are described as being efficacious in inducing immunity and reducing acute replication and establishment of latency of the challenged wild-type virus in mice. Nguyen et al describe replication-defective mutants of HSV-1 that have mutations in the essential genes encoding infected cell protein 8 ("ICP8") or ICP27 [J. Virol. 66:7067–7072 (1992)]. The ICP8 mutant (d301) expresses the products of the α and β genes while the ICP27 mutant (n504) expresses the products of the α, β, and $\gamma_1$ genes in the cells that the viruses can infect. Both viruses induced antibody responses that were lower than parental (KOS 1.1) virus, but the level induced by the ICP27 mutant was higher than that induced by infection with the ICP8 mutant. Morrison and Knipe later demonstrated that injection of these viruses protected mice against development of encephalitis and keratitis, and decreased the primary replication of virulent challenge virus [J. Virol. 68:689–696 (1994)]. WO95/18852 describes similar replication-defective herpesvirus mutants and WO94/03207 describes vaccines based on these mutants.

Another recombinant virus has been described that has a deletion in the glycoprotein H (gH) coding region [Forrester et al, J. Virol. 66:341–348 (1992); WO92/05263]. This virus forms virions after infection of non-helper cells, but the viruses fail to infect in a subsequent round. Inoculation of mice with the gH deletion virus resulted in a more rapid clearance of the wild-type challenge virus compared to vaccination with chemically-inactivated virus [Farrell et al, J. Virol. 68:927–932 (1994)]. Inoculation of guinea pigs with the gH deleted recombinant virus resulted in reduced primary vaginal disease and reduced recurrences [McLean et al, J. Infect. Dis. 170:1100–1109 (1994)].

Most viruses encode proteinases that function in the processing of viral proteins during infection [W. G. Dougherty and B. L. Semler, Microbiological Reviews, 57:781–822 (1993)]. Biological and biochemical studies have shown that HSV-1 possesses a proteinase that can process another viral protein, the capsid assembly protein (also known as p40, ICP35 and VP22a). Similar proteinases are encoded in the genome of other members of the Herpesviridae. This family of DNA viruses includes HSV-1, HSV-2, human and simian cytomegalovirus (HCMV, SCMV), varicella-zoster virus (VZV), Epstein-Barr virus (EBV), human herpesvirus types -6, -7, and -8 (HHV-6, HHV-7, and HHV-8), pseudorabies virus (PRV), bovine herpesvirus (BHV), equine herpesvirus (EHV), and rhinotracheitis virus, among others.

Early work by Preston et al, [J. Virol. 45:1056–1064 (1983)] showed that a temperature-sensitive (ts) mutant in HSV-1 (ts1201) failed to cleave the capsid assembly protein to its lower molecular weight forms at the nonpermissive temperature. This mutant also failed to package viral DNA. By marker rescue, the defect was mapped to a region of the genome in what is now known as the UL26 open reading frame (ORF) [McGeoch et al, J. Gen. Virol. 69:1531–1574 (1988)]. Subsequent analysis showed that two transcripts initiate in the UL26 region, a primary transcript of about 2.1 kb which encodes a protein of 635 amino acids, and a more abundant transcript which is initiated within the UL26 ORF, about 1000 nucleotides 3' of the primary transcript initiation. This smaller transcript encodes a predicted protein of 329 amino acids and is 3' coterminal with the larger 80 kDa ORF encoded by the larger transcript [F. Y. Liu and B. Roizman. J. Virol. 65:206–212 (1991)]. The defect in the ts1201 mutant maps in the 5' region of the longer transcript which has been shown to encode a proteinase activity in HSV-1 [F. Y. Liu and B. Roizman. J. Virol. 65:5149–5156 (1991)] or in simian cytomegalovirus [Welch et al, Proc. Natl. Acad. Sci. U.S.A. 88:10792–10796 (1991)].

Superinfection/transient expression [F. Y. Liu and B. Roizman. J. Virol. 65:5149–5156 (1991)], transient expression [Welch et al, Proc. Natl. Acad. Sci. U.S.A. 88:10792–10796 (1991)], and infection [Preston et al, Virol. 186:87–98 (1992)] studies with the protease domain and the capsid assembly protein domain showed that the proteinase cleaves the capsid assembly protein near its carboxyl terminus. Further studies with the proteins produced in *E. coli* confirmed that the full-length protein of the UL26 ORF is capable of cleaving itself at two sites as well as cleaving the capsid assembly protein [Deckman et al, J. Virol. 66:7362–7367 (1992)]. DiIanni et al later located the cleavage sites between amino acids 247/248 and 610/611 of the UL26 ORF [J. Biol. Chem. 268:2048–2051 (1993)].

Although the results with ts1201 suggest that the defect in the virus is in its ability to cleave the capsid assembly protein and subsequent encapsidation of DNA, it is not known whether this phenotype is the result of a defect in the protease activity per se, or whether the 5' region of the UL26 ORF encodes some other functions required for capsid assembly and maturation. The processed proteinase domain of the 80 kDa precursor (designated as "VP24" or "$N_o$") has been identified in B-capsids [Davison et al, J. Gen. Virol. 73:2709–2713 (1992)] and is retained in A-capsids and C-capsids [F. J. Rixon, Structure and Assembly of Herpesviruses, in Seminars in Virology, vol. 4, 135–144, (A. J. Davison, ed. 1993)] suggesting a structural role for this domain. B-capsids are immature capsids in the nucleus of the infected cell that contain the capsid assembly protein, but not viral DNA. These capsids are thought to be the precursors of A-capsids which fail to package DNA and C-capsids which package DNA with concomitant loss of the capsid assembly protein [B. Roizman and A. Sears, Herpes Simplex Viruses and Their Replication, in Human Herpesviruses, 11–68, (B. Roizman, R. J. Whitley, and C. Lopez, eds. 1993)]. Gao et al constructed and characterized a null mutant virus ("m100") that contains a deletion within the protease domain of the HSV-1 UL26 gene [J. Virol. 68:3702–3712 (1994)]. The mutant virus could be propagated on a complementing cell line but not on noncomplementing Vero cells, indicating that the protease domain of UL26 is essential for viral replication in cell culture. DNA replication occurred at near wild-type levels, but the viral DNA was not processed to unit genome length or encapsidated.

We have generated a recombinant virus to further investigate the role of this domain with respect in vivo effects. The recombinant virus is avirulent in vivo and induces immunity to challenge by wild-type HSV-1.

DESCRIPTION OF THE INVENTION

Figure 1:
FIG. 1 shows the construction of four plasmids. (A) Plasmid pMON15831a contains a 3.4 kb KpnI fragment of HSV-1 ("KOS") upstream of the SV40 polyadenylation signal. (B) Plasmid pMON15840 has a UL26 ORF downstream of the herpesvirus ICP6 promoter region. Translation of UL26 begins at methionine 10. (C) Sequence of the multiple cloning site inserted into the BspEI/BclI-digested pMON27005. (D) Plasmid pMON15835 contains an ICP6-β-glucuronidase cassette inserted into the BclI site of pMON27005. The UL26 ORF is shown as the stippled box, the ICP6 promoter region is shown as the hatched box. The plasmids are not drawn to scale. Abbreviations: "K", KpnI; "B", BsgI; "S", SmaI.
Figure 1:
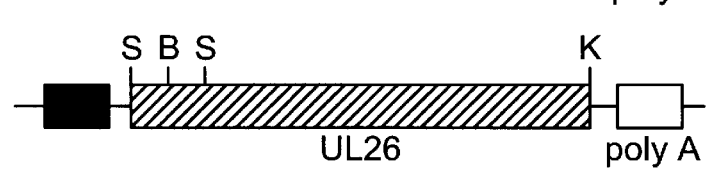
Figure 1:
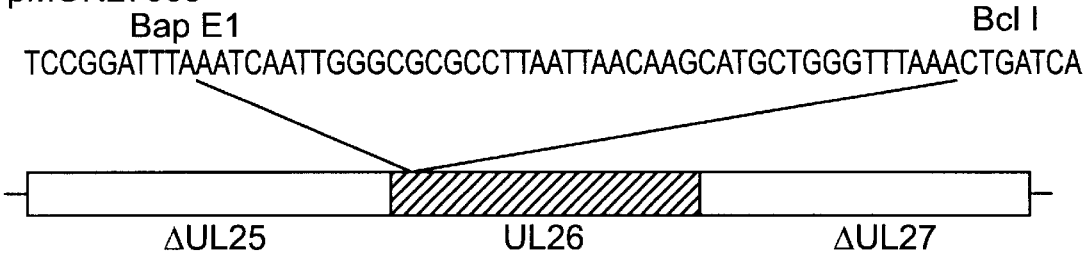
Figure 1:
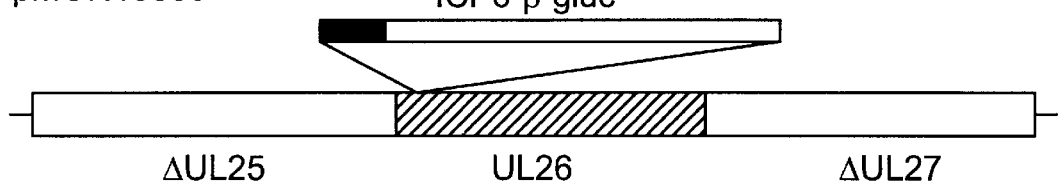

The present invention describes a vaccine comprising an assembly-deficient herpesvirus. Preferably, the herpesvirus contains an inactivated form of an essential protease gene. More preferably, the protease is required for the processing and assembly of immature, noninfectious capsid particles into mature, infectious capsid particles.

The protease gene can be inactivated by a method selected from deletion, insertion, substitution and any combination of deletion, insertion, or substitution. Preferably, the protease gene is inactivated by deletion of viral DNA and insertion or substitution of nonviral (heterologous) DNA. More preferably, the essential protease gene is inactivated by deletion of viral DNA and insertion of nonviral (heterologous) DNA.

Preferably, the inactivated protease gene is selected from HSV-1 UL26, HSV-2 UL26, and HCMV UL80. More preferably, the protease is encoded by HSV-1 UL26.

The invention includes herpesviruses selected from HS-1, HSV-2, HCMV, SCMV, VZV, EBV, HHV-6, HHV-7, HHV-8, PRV, BHV and EHV. Preferably, the virus is HSV-1 or HSV-2. More preferably, the virus is HSV-1. Preferably, the vaccine comprises the assembly-deficient mutant virus designated HSV/UL26/β-gluc.

Preferably, the vaccine comprises a dose between about 10 and about $10^6$ plaque-forming units of said assembly-deficient herpesvirus.

Additionally, the present invention describes a method of manufacturing a vaccine comprising an assembly-deficient herpesvirus, by preparing stocks of the virus in a recombinant cell line capable of generating properly assembled virus. Preferably, the method of manufacturing a vaccine uses a virus selected from HSV-1, HSV-2, HCMV, SCMV, VZV, EBV, HHV-6, HHV-7, HHV-8, PRV, BHV, and EHV. More preferably, the method of manufacturing a vaccine uses virus selected from HSV-1 and HSV-2. Even more preferably, the method of manufacturing a vaccine uses a virus derived from HSV-1.

The present invention also describes a use of an assembly-deficient herpesvirus in a preparation of a vaccine.

Additionally, the present invention describes a method of immunizing a susceptible mammal against a herpesvirus by administering a vaccine comprising an assembly-deficient herpesvirus. Preferably, the susceptible mammal is selected from human, monkey, cow, horse, sheep, and pig. More preferably, the mammal is human.

The present invention also describes a mutant herpesvirus containing an inactivated form of an essential protease gene required for the processing and assembly of immature, noninfectious capsid particles into mature, infectious capsid particles, said essential protease gene is inactivated by deletion of viral DNA and insertion of nonviral (heterologous) DNA.

Preferably, the essential protease gene is inactivated by deletion of a portion of the essential protease gene and insertion of a nonviral (heterologous) DNA segment comprising a reporter gene under the control of an inducible promoter. More preferably, the essential protease gene is the HSV-1 UL26 gene. More preferably, the inducible promoter is the HSV-1 ICP6 (UL39) promoter. Even more preferably, the nonviral (heterologus) DNA segment comprises the gusA gene encoding E. coli beta-glucuronidase under the control of an HSV-1 ICP6 (UL39) promoter.

The present invention additionally describes a recombinant host cell line expressing an essential protease gene under the control of an inducible promoter. Preferably, the recombinant host cell line is derived from a mammalian source. More preferably, the recombinant host cell line is derived from a rodent source. Even more preferably, the recombinant host cell line is BHK-21. Preferably, the inducible promoter is a herpesvirus promoter. More preferably, the inducible promoter is the HSV-1 ICP6 (UL39) promoter.

The present invention also describes a method of making mutant herpesviruses by introducing the virus into a recombinant host cell line and recovering mature viral particles harboring the mutant viral genome.

Definitions

The phrase "assembly-deficient" is intended to mean that the virus is able to replicate its DNA, but is unable to complete the steps of cleaving that DNA into genome-length pieces and packaging that DNA into viral capsids.

The phrase "mature virion" is intended to mean a viral particle capable of infection in a susceptible host or cell type. The phrase "nonviral (heterologous) DNA" is intended to mean DNA that is not derived from a herpesvirus genome. The phrase "nonessential gene" is intended to mean a gene that can be disrupted by deletion, insertion, substitution, or a combination of deletion, substitution, and insertion of other DNA, and that a recombinant virus containing this disrupted gene can propagate in cultured cells that do not express nondisrupted copies of the same gene. The phrase "essential gene" is intended to mean a gene that is not a nonessential gene. The phrase "essential viral protease gene" is intended to mean an essential viral gene that encodes a protease.

EXPERIMENTAL

Baby hamster kidney cells (BHK-21) were obtained from American Type Culture Collection (ATCC) (Rockville, Md.) and were cultured in Dulbecco's modified Eagle's media supplemented with 10% fetal bovine sera (JRH Biosciences, Lenexa, Kans.), 2 mM additional L-glutamine (JRH Biosciences) and 100 µg-units/ml of penicillin-streptomycin (JRH Biosciences). HSV-2 strain MS was obtained from ATCC and HSV-1 strain 17 was obtained from Dr. R. Lausch, University of South Alabama. Viral DNA was isolated and purified according to D'Aquila and Summers [J. Virol. 61:1291–1295 (1987)] for stock quantities and according to DeLuca et al [J. Virol. 52:767–776 (1984)] and Rader et al [J. Gen. Virol. 74:1858–1869 (1993)] for rapid Southern blot evaluation.

To generate cell lines that complement the defect in the UL26 gene, BHK-21 cells were cotransfected with 10 µg plasmid DNA containing the complementing sequences (see below) and 1 µg SV2neo [P. J. Southern and P. Berg. J. Mol. Appl. Genet. 1:327–341 (1982)] using LipofectAmine Reagent (GIBCO/BRL/Life Technologies, Inc., Grand Island, N.Y.) according to the manufacturer's instructions. After two days, cells were treated with trypsin and diluted into media containing 400 µg/ml G418 (Geneticin, Gibco/BRL/Life Technologies, Inc.). Individual colonies were isolated and expanded for determination of helper function.

Two plasmids were made for engineering a cell line that would complement a protease defective HSV-1. First, a 3.4 kb KpnI fragment from HSV-1 (KOS) (from P. Olivo, Washington University) containing the entire UL26 promoter region and open reading frame (ORF) was subcloned into the KpnI site of pMON3327 [Highkin et al, Poultry Science 70:970–981 (1991)] such that the SV40 polyadenylation signal is 3' to the UL26 ORF. This plasmid was designated pMON15831a (FIG. 1). The second plasmid consists of the UL26 ORF under control of the HSV-1 ICP6 (UL39) promoter region. This plasmid was synthesized in several steps. First, the 320 bp SmaI fragment containing the 5' end of the UL26 ORF starting at nucleotide 18 was subcloned into the SmaI site of pUC18 resulting in pMON15838. The 1642 bp BsgI-KpnI fragment from pMON27010 was inserted into BsgI-KpnI digested pMON15838 to yield pMON15839. pMON27010 has the 3.4 kb KpnI fragment from HSV-1 (strain 17) in pUC18. The 1956 bp EcoRI-HindIII fragment was isolated from pMON15839 and the ends were filled-in using Klenow polymerase before ligating to pMON15834 which had been digested with BamHI and filled in as above. The resulting plasmid was designated pMON15840 (FIG. 1). Plasmid pMON15834 has the filled-in 633 bp XhoI-SnaBI fragment of HSV-1 (strain 17) that directs the expression of the ICP6 ORF in the SmaI site of pMON3327.

A β-glucuronidase cassette was inserted into the UL26 ORF as follows: The β-glucuronidase cassette under control of the HSV-1 ICP6 promoter region was constructed by isolating a 633 bp XhoI-SnaBI fragment from pMON27002. pMON27002 has the 16,191 bp Sse8387I D fragment from HSV-1 (strain 17) in pNEB193 (New England Biolabs, Beverly, Mass.). The XhoI site was filled-in using Klenow polymerase and was ligated into the filled-in NcoI site in pMON14327 (Luckow et al, J. Virol. 67:4566–4579 (1993)] which contains the glucuronidase gene. The new plasmid is designated pMON15833. The NotI H fragment (6542 bp) containing the HSV-1 (strain 17) UL26 ORF was subcloned into NotI-digested pBS2SKP (Stratagene, La Jolla, Calif.) to generate plasmid pMON27005. pMON27005 was digested with BspEI and BclI. A polylinker containing multiple cloning sites and complementary ends was inserted to create plasmid pMON27026 (FIG. 1). To construct a cassette for recombination with wild-type HSV-1 (strain 17), the 2871 bp ICP6-β-glucuronidase sequences were removed from pMON15833 by BamHI digestion and ligated into BclI-digested pMON27026. The new vector is designated pMON15835 (FIG. 1).

BHK cells were seeded at $4\times10^5$ cells per 60 mm dish one day prior to transfection. One microgram of genomic viral DNA and an equimolar amount of linearized plasmid containing the desired sequence changes were mixed with 25 µg of LipofectAmine in OptiMem media (Gibco/BRL/Life Technologies) and added to the cells for 4 hours. The media was aspirated and replaced by growth media. The transfected cells were completely lysed before the harvesting of the supernatant. Clarified, serially-diluted supernatant (0.8 ml) was plated onto the helper cell line in 60 mm dishes at 37° C. for 60 minutes. The inoculum was removed and the cells were overlaid with a 1% agarose (JRH Biosciences)/ 10% FBS/EMEM (BioWhitaker, Walkersville, Md.). After the formation of visible cytopathic effects, 4 ml Dulbecco's phosphate-buffered saline (JRH Biosciences) containing 300 µg/ml X-gluc (BioSynth AG, Switzerland) and 80 µg/ml neutral red (Sigma, St. Louis, Mo.) were added, and plaques were picked using a Pasteur pipette. For viruses containing the β-glucuronidase gene, blue plaques were selected. For rescued viruses (see below), clear plaques were selected. The viruses were plaque-purified three times or purified by limiting dilution. Purified virus was isolated and the DNA was analyzed by restriction enzyme analysis and Southern blotting [Maniatis et al, Molecular Cloning, A Laboratory Manual (1982)].

Analysis of the clear plaque virus in the blue plaque virus stock was done by the polymerase chain reaction (PCR) (Saiki et al, Science. 239:487–491 (1988)]. Two oligonucleotides that flanked the unique BsgI site in the HSV-1 (strain 17) UL26 ORF were synthesized (Genosys, The Woodlands, Tex.). The forward primer was identical to nucleotides 50,913 to 50,932 of the HSV genome [5'-GGGCGAGTTGGCATTGGATC-3', McGeoch et al, J. Gen. Virol. 69:1531–1574 (1988)]. The reverse primer was complementary to sequences 51,195 to 51,175 of the HSV-1 genome (5-AGACCGAGGGCAGGTAGTT-3'). Virus was extracted with phenol:chloroform and the viral DNA was ethanol-precipitated. The PCR was carried out using the GeneAmp PCR kit (Perkin-Elmer-Cetus, Norwalk, Conn.). The reaction products were analyzed on 5% polyacrylamide gels.

Peptide antibodies were raised in rabbits against regions corresponding to amino acids 414 through 428. Peptide HSVAs-414 (C-PAAGDPGVRGSGKR) was synthesized by Chiron Mimotopes Pty. Ltd. (Raleigh, N.C.) and purified to greater than 95% purity. HSVAs-414 mapped to the central region of the capsid assembly region of the UL26 and UL26.5 genes. The peptide had a free acid at the C-terminus and was conjugated to diphtheria toxoid at the N-terminus. Rabbits were inoculated with 100 µl of 1 µg/ml of protein mixed with an equal volume of Freund's complete adjuvant, boosted with the same material in Freund's incomplete adjuvant at 4 week intervals beginning at week 2, and bled 10 and 17 days after boosting.

Cells were seeded in wells of six-well dishes at $5 \times 10^5$ cells/well. The next day, cells were infected with a multiplicity of infection (MOI) of 5 pfu/cell for 60 minutes at 37° C. with occasional gentle rocking. The inoculum was aspirated and growth media was added. At 18 hours post infection, the media was aspirated and 400 µl of 1× Protein Disruption Buffer (Novex, San Diego, Calif.) containing 10% β-mercaptoethanol were added. Proteins were separated on 14% Tris-glycine SDS-polyacrylamide gels (Novex) for 1.5 hours at 125 volts. The gels were incubated for 10 minutes in 1× Transfer Buffer (Novex) and blotted to Immobilon-P membranes (Novex) for 1–2 hours at 30 volts. The membranes were incubated in 1× Tris-buffered saline containing Tween 80 (TTBS), supplemented with 5% powdered milk for at least one hour (typically overnight). The blot was rinsed twice with TTBS for 15 minutes, and incubated with primary antibody for 1 hour at a dilution of 1/1000. The blot was rinsed twice with TTBS for 15 minutes before incubating with secondary antibody (alkaline phosphatase conjugated goat anti-rabbit antibody, Promega, Madison, Wis.) for 1 hour at a dilution of 1/4000. The alkaline phosphatase was visualized by incubating the blot in nitro blue tetrazolium (NBT)/5-bromo-4-chloro-3-indolyl phosphate (BCIP) (Promega) for 5 to 15 minutes, and the reaction stopped by rinsing extensively in $H_2O$.

Viral replication was examined by multistep growth analysis on the BHK/UL26 helper line and on BHK cells that did not contain the helper function but were G418-resistant (BHK/C2). Cells ($1 \times 10^5$) were seeded in wells of a 24-well plate and infected with an MOI of 0.1 plaque-formingunits (pfu) per cell. At various times post infection, the infected cells were subjected to three rounds of freeze-thawing [Tengelsen et al, J. Virol. 67:3470–3480 (1993)] and the lysates were titered on the BHK/UL26 helper line.

To generate cell lines capable of supporting replication recombinant viruses with a deletion and insertion within the UL26 open reading frame, BHK cells were cotransfected with pMON15831a which has the 3.4 kb KpnI fragment of HSV-1 (KOS) 5' to the SV40 polyadenylation signal (FIG. 1) and SV2neo. G418-resistant cells were isolated and shown by Southern blot analysis to contain the HSV-1 KpnI fragment. To determine which cell line would express the UL26 gene products, the cell lines were infected with HSV-2 (MS) to stimulate the UL26 promoter in the cell. HSV-1-specific anti-peptide antisera, generated by inoculating rabbits with the peptide HSVAs-414 conjugated to diphtheria toxin, was used to identify expression of the cellular UL26 gene products (data not shown). This cell line, designated BHK/UL26/8, was used for generation of recombinant viruses. A G418-resistant cell line which was cotransfected with pMON3327 and SV2neo serves as a control and is designated BHK/C2. An additional helper cell line (BHK/ UL26 helper) was isolated after the discovery that significant amounts of rescued virus were being generated due to recombination with the KpnI fragment present in BHK/ UL26/8. This second line was transfected with plasmid pMON15840 which has the UL26 ORF behind the ICP6 promoter and lacks the large amount of HSV DNA 5' to the UL26 ORF contained in pMON15831a. Translation from this integrated plasmid began at the methionine at the natural amino acid 10. Candidate cell lines were screened for their ability to support growth of the blue plaque phenotype recombinant virus (see below). A cell line isolated from this latter screening that supports the growth of the UL26 mutant virus was designated the BHK/UL26 helper cell line.

Cell line BHK/UL26/8 was transfected with HSV-1 (strain 17) genomic DNA and plasmid pMON15835 which contains a NotI fragment of HSV-1 (strain 17) with a deletion in the protease domain of the UL26 ORF and an insertion of the bacterial β-glucuronidase gene under control of the HSV-1 (strain 17) ICP6 promoter (FIG. 1). After cell lysis, the supernatant was serially-diluted on BHK/UL26/8 and blue plaques were identified after 4 to 5 days post infection. The blue plaques were picked and plaque-purified three times. The recombinant virus was designated HSV/ UL26/β-gluc. Plaque purification indicated poor segregation between the blue phenotype recombinant virus and a clear plaque phenotype virus which appeared to have a growth advantage, even on the helper cell line.

To determine the genotype and source of the clear plaque virus, DNA amplification was performed on cell-free viral DNA from the mixed culture of blue and clear plaque phenotype viruses. Amplification of a 283 bp fragment indicated the presence of wild-type virus in the stock. The PCR product was digested with BsgI, which cuts the fragment from wild-type (strain 17) DNA, but does not cut the fragment from wild-type (strain KOS) DNA, which is the source of DNA in the helper cell (data not shown). Lack of digestion of the PCR product by BsgI indicated that the wild-type virus was actually a revertant generated by recombination between the blue plaque phenotype virus and the UL26 sequences in the helper cell line. The rescued virus was designated HSV/UL26/res.

In order to generate a more pure stock of HSV/UL26/β-gluc, a new helper cell line (BHK/UL26 helper) was isolated in which the amount of HSV DNA sequence 5' to the UL26 ORF was eliminated and replaced with the ICP6 promoter region fragment (pMON15840, FIG. 1). Propagation of HSV/UL26/β-gluc on this cell line resulted in only the blue plaque phenotype.

Figure 2:
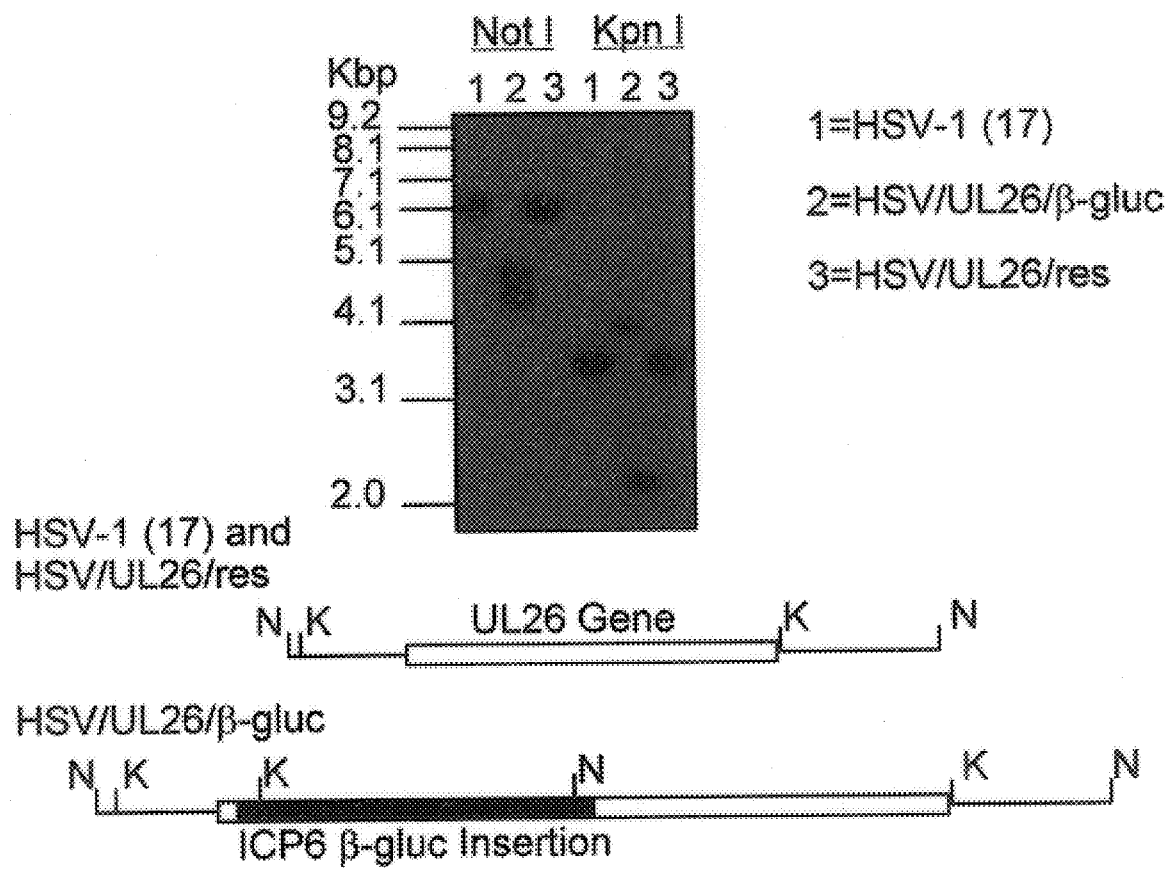
FIG. 2 shows the Southern blot analysis of recombinant viruses. Viral DNA was digested with NotI or KpnI, transferred to nitrocellulose and hybridized to an α-32P-dGTP-labeled 3.4 kb KpnI fragment shown in FIG. 1A. Schematics show the restriction maps of the viruses. The hatched region in the UL26 deletion schematic is the ICP6-β-glucuronidase insertion in the protease domain. Lane 1, HSV-1 ("17"); Lane 2, HSV/UL26/β-gluc; Lane 3, HSV/UL26/res. Abbreviations: "N", NotI; "K", KpnI.

Viral DNA from wild-type (strain 17), HSV/UL26/β-gluc and the rescued virus was digested with NotI or KpnI. The digested DNA was analyzed by Southern blot analysis after probing with a restriction fragment containing the full length UL26 open reading frame and 5' flanking sequences. The results showed the expected pattern of digestion (FIG. 2). Wild-type and rescued virus showed the same pattern as expected with both NotI (6.3 kb) and KpnI (3.4 kb) digestion (Lanes 1 and 3). Deletion of a small region of the UL26 ORF and insertion of the β-glucuronidase gene resulted in addition of a new NotI site (resulting in predicted 4.8 and 4.4 kb fragments) and a new KpnI site (resulting in a 4.0 and 2.1 kb fragments) (Lane 2) in HSV/UL26/β-gluc.

Figure 3:
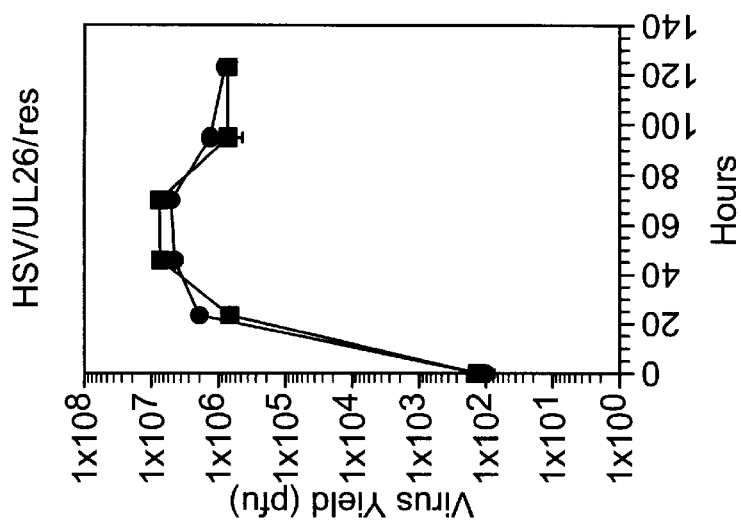
FIG. 3 is a graphical representation which shows the multistep growth curves of mutant viruses. BHK/UL26 helper or BHK/C2 cells were infected at an MOI of 0.1. Cells were harvested at various time points and the virus was titered on BHK/UL26 helper cells. Circles represent virus from BHK/UL26 helper cells and squares represent virus from BHK/C2 cells. The error bars represent the ranges of duplicate determinations.
Figure 3:
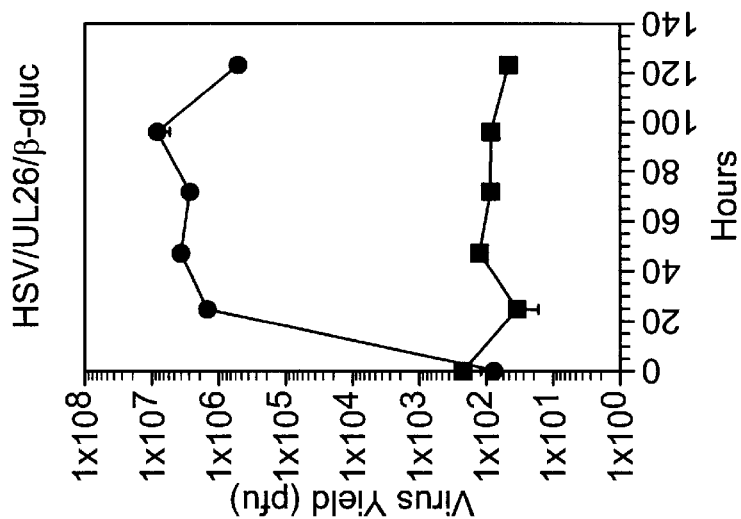
Figure 3:
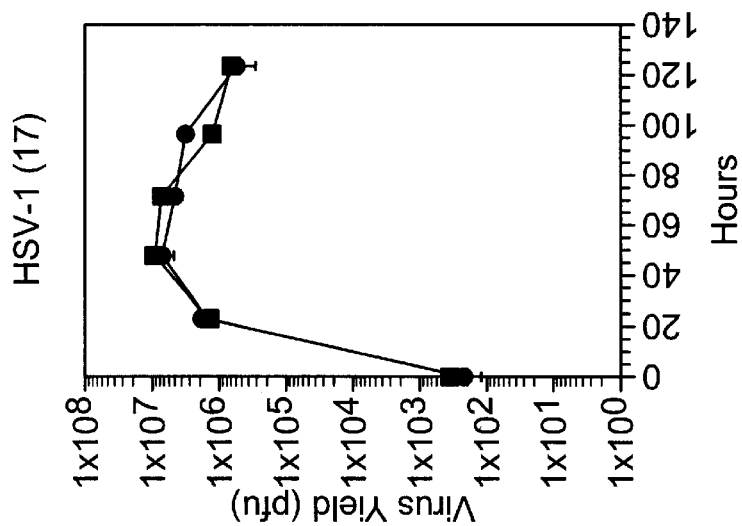

Growth curves were determined for the viruses on the different cell lines. At various times post infection, the cells were harvested and freeze-thawed three times before plating on BHK/UL26 helper cells. The results indicated that HSV/UL26/β-gluc failed to replicate in BHK/C2 cells but grew with wild-type kinetics on the BHK/UL26 helper cell line. The wild-type (strain 17) HSV-1 and the rescued virus replicated to identical titers and at identical rates on both BHK/C2 and the BHK/UL26 helper cell lines (FIG. 3).

Figure 4:
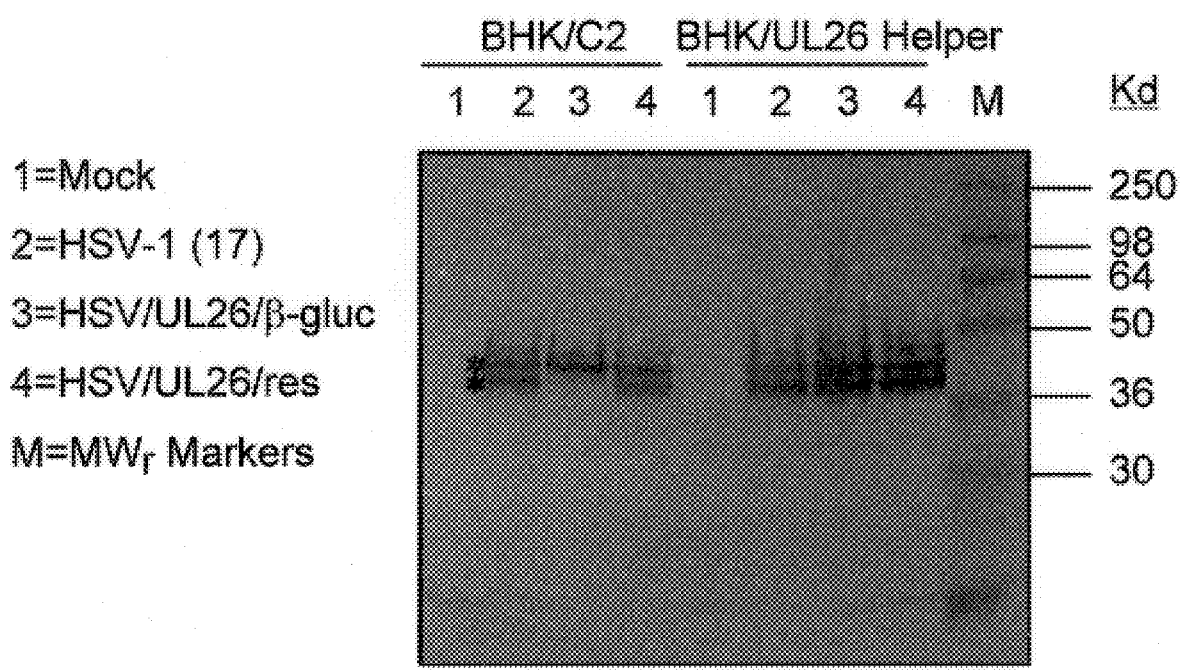
FIG. 4 shows the capsid assembly protein processing results. BHK/C2 and BHK/UL26 helper cells were infected with an MOI of 5 for 18 hours. Cells were harvested and proteins were separated on a 14% denaturing SDS-polyacrylamide gel, transferred to Immobilon membrane, and probed with antisera generated against a peptide of the HSV-1 capsid assembly protein (HSVAs-414). The open star indicates the major unprocessed assembly protein and the closed star indicates the processed form. Lane 1, mock infected cells; Lane 2, wild-type HSV-1; Lane 3, HSV/UL26/β-gluc; Lane 4, HSV/UL26/res.

Since it has been shown by transient transfection experiments in mammalian cells, bacteria and ts1201 that certain mutations in the 5' region of UL26 fail to cleave the capsid assembly protein [reviewed in Gao et al, J. Virol. 68:3702–3712 (1994)], HSV/UL26/β-gluc was used to infect BHK/C2, BHK and BHK/UL26 helper cells at an MOI of 5. At 18 hours post infection, the cells were lysed in SDS-PAGE sample buffer and proteins separated on a 14% SDS-PAGE gel. After transfer to Immobilon P membranes, the blots were incubated in antisera against the HSV-1 capsid assembly protein. The results are shown in FIG. 4. Infection of BHK/C2 cells by HSV/UL26/β-gluc resulted in a failure to process the capsid assembly protein to a lower molecular weight form. Infection of BHK/helper cells by HSV/UL26/β-gluc showed that the capsid assembly protein was appropriately processed. The rescued recombinant virus (HSV/UL26/res) processed the capsid assembly protein in both cell lines as did wild-type HSV-1 (lanes 2 and 4). The capsid assembly protein was made at normal levels during infection in both helper and non-helper cells but is not cleaved in the non-helper cells. The HSV/UL26/β-gluc recombinant fails to process the capsid assembly protein and has restricted growth.

Female Swiss-Webster mice (12–14 grams, Charles Rivers Laboratories, Wilmington, Mass.) were inoculated with virus intraperitoneally or subcutaneously with 100 μl volumes. Subcutaneous inoculations were delivered on the dorsal side near the base at the tail after brief $CO_2/O_2$ treatment of the mice. Virus was resuspended in DMEM containing 5% FBS unless otherwise noted. Food and water were given ad libitum. Mice were euthanized if they became moribund due to paralysis.

Figure 5:
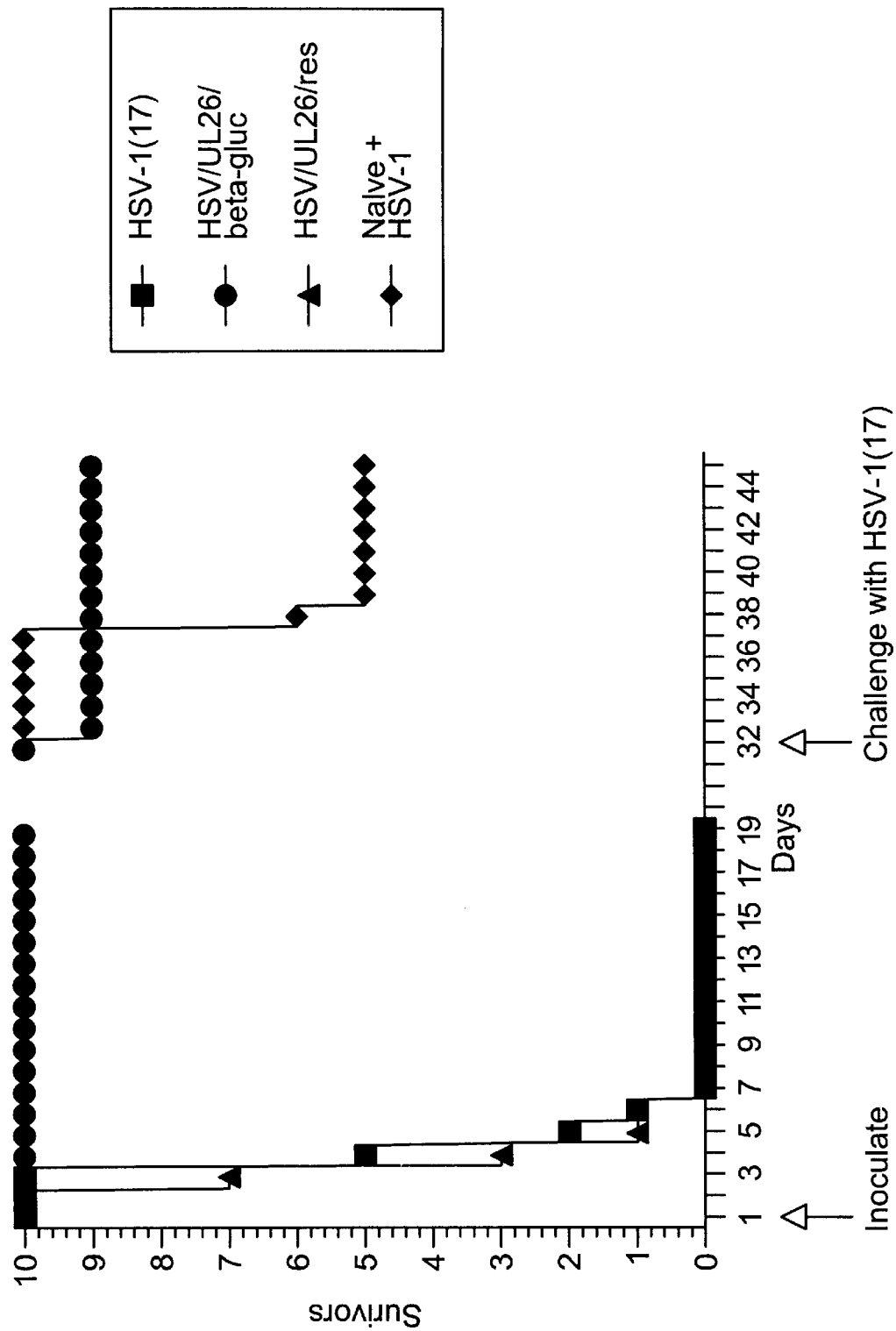
FIG. 5 is a graphical representation which shows the viral challenge of mice. Mice were inoculated intraperitoneal (i.p.) with $6 \times 10^5$ pfu of each virus and scored for mortality. The survivors and control mice (age-and sex-matched) were challenged with another dose of wild-type virus on day 32.

Mice were inoculated i.p. with $6 \times 10^5$ pfu (as determined on the helper cell line) of either the wild-type (strain 17) HSV, HSV/UL26/β-gluc, or the rescued virus in a 100 μl volume. As shown in FIG. 5, mice infected with wild-type (strain 17) or the rescued virus died by day 7 post infection. All mice infected with HSV/UL26/β-gluc survived. The animals that originally received HSV/UL26/β-gluc were challenged with wild-type HSV-1 (strain 17), i.p., at the same dose given initially. Age- and sex-matched naive mice were also inoculated. One of the HSV/UL26/β-gluc infected mice was found dead about 16 hours post infection with the wild-type virus. Death was probably not related to the virus since it occurred so quickly after infection. The other 9 mice survived the wild-type virus challenge. The naive mice were susceptible to wild-type virus infection although it took longer for the virus to cause morbidity and mortality (FIG. 5).

In a second experiment, mice were inoculated i.p. with ten-fold serial dilutions of HSV/UL26/β-gluc starting at the same inoculum used in the initial experiment. On day 39, the mice were challenged i.p. with $6 \times 10^6$ pfu of HSV-1 (strain 17). This dose of wild-type virus was 10-fold higher than that in the initial experiment and resulted in 90% death in the mice that were initially inoculated with DMEM/5% FBS (Table 1, mock-infected set). Again, within 16 hours, 6 mice were found dead. Two of these were in the set that were previously inoculated with 10 pfu of HSV/UL26/β-gluc and 4 were in the set that were previously given $1 \times 10^5$ pfu of HSV/UL26/β-gluc. There was a significant difference among the six survival curves (p<0.02, log rank test). The data suggests that mice that were inoculated with HSV/UL26/β-gluc survived in a dosedependent manner (Table 1). The survival curves of the mice receiving the highest dose of HSV/UL26/β-gluc were statistically different from the mock group (p=0.023, log rank test).

TABLE 1

| HSV/UL26/β-gluc | % Survival* |
|---|---|
| mock | 10 |
| $6 \times 10^1$ pfu | 12.5 |
| $6 \times 10^2$ pfu | 30 |
| $6 \times 10^3$ pfu | 60 |
| $6 \times 10^4$ pfu | 50 |
| $6 \times 10^5$ pfu | 83.3 |

*Survival determined on day 20 after i.p. challenge with $6 \times 10^6$ pfu of wild-type HSV-1 (strain 17). N = 10 for all groups except for the $6 \times 10^1$ (N = 8) and $6 \times 10^5$ (N = 6) due to the early death.

Figure 6A:
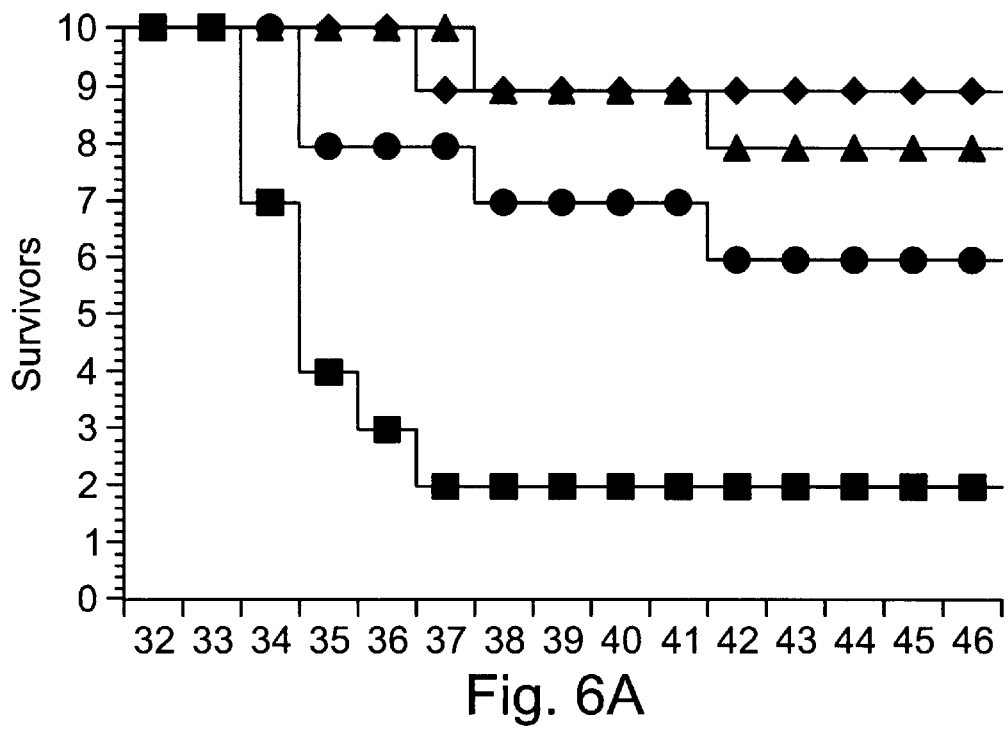
FIG. 6 is a graphical representation which shows i.p. or subcutaneous (s.q.) inoculation of mice inoculated with media or $10^2$, $10^4$, or $10^6$ pfu of HSV/UL26/β-gluc. Mice were inoculated on day 1 either i.p. (A) or s.q. (B). On day 31 the nice were challenged with $10^7$ pfu of wild-type HSV-1 given i.p.
Figure 6B:
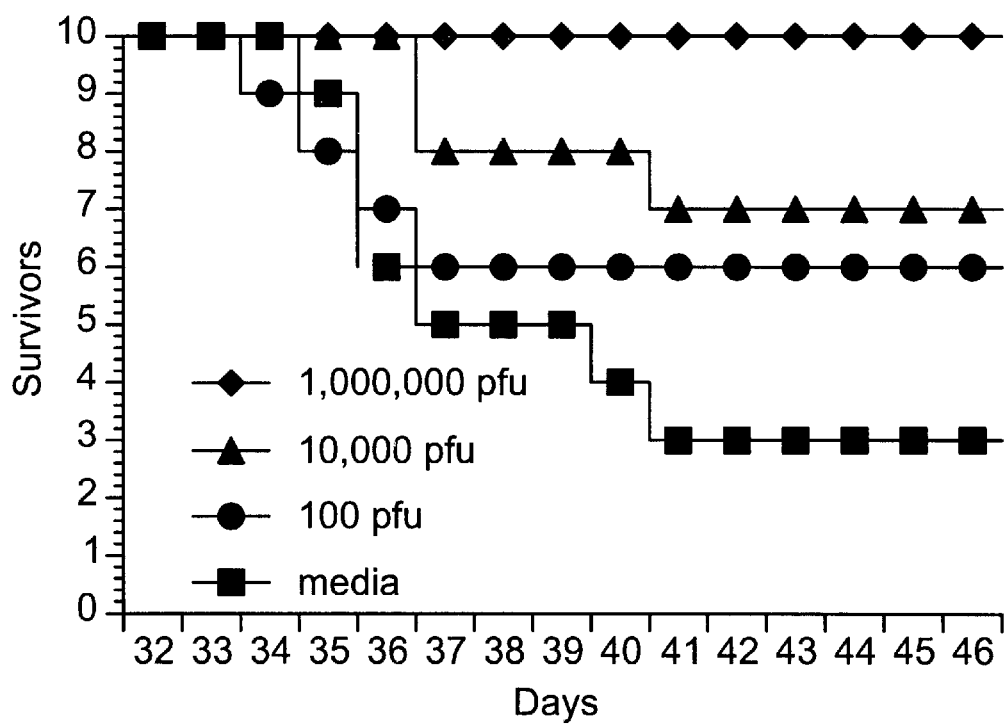

In a third experiment, virus stocks were prepared as previously but were resuspended in DMEM without any FBS. Sets of ten mice were inoculated with DMEM alone or with increasing doses of HSV/UL26/β-gluc by either i.p. or s.q. routes. After one month, all mice were challenged with $10^7$ pfu of wild-type virus by i.p. inoculation. Some controls for rapid death included animals that received i.p. media then challenged with i.p. media, HSV/UL26/β-gluc and then media or, HSV/UL26/β-gluc and then challenged with HSV/UL26/β-gluc. None of these animals died during the course of the experiment. None of the experimental animals died within 24 hours of challenge. of these, 90 animals had received two inoculations of virus and one would expect about 10–12% to have died rapidly. The results with the experimental groups are shown in FIGS. 6A and 6B. There was a significant difference among the survival curves for both the i.p. (p<0.01) and s.q. (p<0.01) inoculations (log rank test). Regression analysis shows that there is a dose-dependent effect of HSV/UL26/β-gluc on survival (p<0.05, Cochran-Armitage test) for both groups.

It is expected that this virus would have reduced efficiency and reactivate poorly, if at all. The fact that the mutation effects a late gene function suggests that the recombinant virus may be more efficacious in inducing immunity than viruses that have deletions in immediate early or early genes. The assembly-defective HSV/UL26/β-gluc virus is a member of a new class of vaccine candidates with a defect in late gene activity.

It is anticipated that the defect in the essential gene described in an assembly-deficient virus can be incorporated in a virus with other mutations in essential or nonessential genes. Such genes, like ICP47 of HSV-1, may modulate the host's ability to mount an immune reaction to the virus [Hill et al, Nature 375:411–415 (1995); Früh et al, Nature 375:415–417 (1995)].

The vaccines of the present invention can be of a lyophilized form or suspended in a pharmaceutically-acceptable carrier. Suitable suspensions can include phosphate buffer, saline, glucose, inactivated serum, excipients, and adjuvants. The vaccine can be prepared and used according to standard techniques well known in the art [reviewed in R L. Burke, Seminars in virology, 4:187–197, (1993)]. The effective dose may also be determined by standard techniques well known in the art. Generally, vaccines are formulated in a suitable sterilized buffer and administered by intradermal, intramuscular, or subcutaneous injection at a dosage of between $10^3$ and $10^9$ pfu/kg. The vaccine can also be formulated for oral or ocular administration in vehicles known in the art.

The foregoing detailed description is given to facilitate clearness of understanding only, and no unnecessary limitations are to be understood therefrom, as modifications within the scope of the invention will be obvious to those skilled in the art.

What is claimed:

1. A vaccine comprising an assembly-deficient herpesvirus wherein said herpesvirus contains an inactivated form of an essential protease gene.

2. The vaccine of claim 1 wherein said essential protease gene is required for the processing and assembly of immature, noninfectious capsid particles into mature, infectious capsid particles.

3. The vaccine of claim 1 wherein said herpesvirus is selected from HSV-1, HSV-2, HCMV, SCMV, VZV, EBV, HHV-6, HHV-7, HHV-8, PRV, BHV and EHV.

4. The vaccine of claim 3 wherein said herpesvirus is HSV-1 or HSV-2.

5. The vaccine of claim 3 wherein said herpesvirus is HSV-1.

6. The vaccine of claim 2 wherein said essential protease gene is selected from HSV-1 UL26, HSV-2 UL26, and HCMV UL80.

7. The vaccine of claim 6 wherein said essential protease gene is HSV-1 UL26.

8. The vaccine of claim 1 wherein said essential protease gene is inactivated by a method selected from the group consisting of deletion of DNA, insertion of DNA, substitution of DNA, deletion and insertion of DNA, deletion and substitution of DNA, and insertion and substitution of DNA.

9. The vaccine of claim 8 wherein said essential protease gene is inactivated by deletion of viral DNA and insertion of nonviral (heterologous) DNA.

10. The vaccine of claim 1 comprising between about 10 and about $10^6$ plaque-forming units of said herpesvirus as determined on a helper cell line.

11. The vaccine of claim 1 wherein said assembly-deficient herpesvirus comprises the strain designated HSV/UL26/β-gluc.

12. A method of immunizing a mammal against a herpesvirus by administering a vaccine of claim 1 in a pharmaceutically-acceptable carrier.

13. The method of claim 12 where the mammal is selected from human, monkey, cow, horse, sheep and pig.

14. The method of claim 13 where the mammal is human.

* * * * *